(12) United States Patent
Barbera-Guillem et al.

(10) Patent No.: US 6,261,779 B1
(45) Date of Patent: Jul. 17, 2001

(54) NANOCRYSTALS HAVING POLYNUCLEOTIDE STRANDS AND THEIR USE TO FORM DENDRIMERS IN A SIGNAL AMPLIFICATION SYSTEM

(75) Inventors: Emilio Barbera-Guillem, Powell; M. Bud Nelson, Worthington; Stephanie L. Castro, Columbus, all of OH (US)

(73) Assignee: Bio-Pixels Ltd., Westerville, OH (US)

( * ) Notice: Subject to any disclaimer, the term of this patent is extended or adjusted under 35 U.S.C. 154(b) by 0 days.

(21) Appl. No.: 09/437,076

(22) Filed: Nov. 9, 1999

Related U.S. Application Data
(60) Provisional application No. 60/107,828, filed on Nov. 10, 1998.

(51) Int. Cl.⁷ .................................................. C12P 19/34
(52) U.S. Cl. ................................................. 435/6; 435/91.2
(58) Field of Search ........................................ 435/6

(56) References Cited

U.S. PATENT DOCUMENTS

| | | |
|---|---|---|
| 5,484,904 | 1/1996 | Nilsen et al. . |
| 5,487,973 | 1/1996 | Nilsen et al. . |
| 5,990,479 | 11/1999 | Weiss et al. ................... 250/307 |

FOREIGN PATENT DOCUMENTS

91/08307 * 6/1991 (WO) .

OTHER PUBLICATIONS

Jacoby, "Quantum dots meet biomolecules", C&EN, 1998, Sep. 28, p. 8.
Emory et al., "Direct observation of size–dependent optical enhancement in single metal nanoparticles", 1998, J. Am. Chem. Soc., vol. 12: 8009–8010.
Chan and Nie, "Quantum dot bioconjugates for ultrasensitive nonisotopic detection", Science, vol. 281: 2016–2018, 1998.
Service, "Semiconductor beacons light up cell structures", Science, 1998, Sep. 25, vol 281:1930–1931.
Bruchez et al., "Semiconductor nanocrystals as fluorescent biological labels", Science, 1998, Sep. 25, vol. 281:2013–2015.

* cited by examiner

*Primary Examiner*—John S. Brusca
*Assistant Examiner*—Jeffrey S. Lundgren
(74) *Attorney, Agent, or Firm*—M. Bud Nelson

(57) ABSTRACT

Provided are compositions and assay kits comprising functionalized nanocrystals having extending therefrom a plurality of polynucleotide strands of known sequence; wherein primary dots are used to operably link to a molecular probe, and secondary dots comprise a plurality of polynucleotide strands which are complemetary to the plurality of polynucleotide strands of the primary dots. Also provided is a method for detecting the presence or absence of target molecule in a sample comprising operably linking primary dots to molecular probe, contacting the complex formed with the sample, contacting the sample with successive additions of secondary dots and primary dots. If target molecule is present in the sample, the primary dots and secondary dots will form dendrimers that can be detected by fluorescence emission.

22 Claims, 7 Drawing Sheets

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 1
gggaaaaaaa aaaaaaaa                                                 18

<210> SEQ ID NO 2
<211> LENGTH: 18
<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 2 gggtttttttt tttttttt                                                 18

<210> SEQ ID NO 3
<211> LENGTH: 18
```

```
-continued

<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 3
gggggggggg ggggggg                                                  18

<210> SEQ ID NO 4
<211> LENGTH: 18
<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 4 gcccccccc ccccccc                                                   18

<210> SEQ ID NO 5
<211> LENGTH: 18
<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 5
ggagagagag agagagag                                                 18

<210> SEQ ID NO 6
<211> LENGTH: 18
<212> TYPE: DNA
<213> ORGANISM: Artificial sequence
<220> FEATURE:
<221> NAME/KEY:
<222> LOCATION:
<223> OTHER INFORMATION: synthesized

<400> SEQUENCE: 6
gtctctctct ctctctct                                                 18
```

NANOCRYSTALS HAVING POLYNUCLEOTIDE STRANDS AND THEIR USE TO FORM DENDRIMERS IN A SIGNAL AMPLIFICATION SYSTEM

This is a nonprovisional patent application which claims the benefit of earlier, provisional patent application Ser. No. 60/107,828 filed Nov. 10, 1998 which is herein substantially incorporated by reference.

FIELD OF INVENTION

This invention relates to novel compositions comprising functionalized nanocrystals. More particularly, the present invention relates to water-soluble nanocrystals which further comprise strands of polynucleotides of a known sequence, and the use of such functionalized nanocrystals to provide signal and signal amplification for detecting target molecules.

BACKGROUND OF THE INVENTION

Nonisotopic detection systems have become a preferred mode in scientific research and clinical diagnostics for the detection of biomolecules using various assays including, but not limited to, flow cytometry, nucleic acid hybridization, DNA sequencing, nucleic acid amplification, immunoassays, histochemistry, and functional assays involving living cells. In particular, while fluorescent organic molecules such as fluoroscein and phycoerythrin are used frequently in detection systems, there are disadvantages in using these molecules in combination. For example, each type of fluorescent molecule typically requires excitation with photons of a different wavelength as compared to that required for another type of fluorescent molecule. However, even when a single light source is used to provide a single excitation wavelength (in view of the spectral line width), often there is insufficient spectral spacing between the emission optima of different fluorescent molecules to permit individual and quantitative detection without substantial spectral overlap. Additionally, conventional fluorescent have limited fluorescence intensity. Further, currently available nonisotopic detection systems typically are limited in sensitivity due to the finite number of nonisotopic molecules which can be used to label a biomolecule to be detected.

Branched DNA or DNA dendrimers have been constructed as a signal amplification tool (see, e.g., U.S. Pat. Nos. 5,487,973, 5,484,904, and 5,175,270). These matrices are comprised of a DNA backbone having DNA arms. For example, matrices are constructed of successive subunits of a double-stranded DNA with single stranded arms on each end. Some of the arms are used to hybridize to a specific oligonucleotide probe, whereas other arms are used to bind to a nonisotopic or isotopic label. While providing for the addition of an relative increase in the number of label molecules as compared to other systems, one disadvantage is that a subunit needs to be custom-synthesized to contain at least one arm consisting of a complementary sequence which is capable of hybridizing to the specific DNA sequence which the user wishes to detect. Additionally, the label molecules are attached or ligated to the outwardly extending ends (tips) of the DNA matrices, rather than as an integral part of the matrix.

Thus, there remains a need for a nonisotopic detection system which (a) can result in generation of a signal comprising fluorescence emission of high quantum yield; (b) can result in signal amplification; (c) is not limited as to the chemical nature of the target molecule to be detected (e.g., versus detection of nucleic acid molecules only); (d) can be used to bind molecular probes of various types (versus binding to oligonucleotide probes only); (e) is preferably universal in terms of detecting target molecules of various sequences; and (f) can result in the simultaneous detection of more than one type of target molecule by utilizing a class of nonisotopic molecules that may be excited with a single excitation light source and with resultant fluorescence emissions with discrete fluorescence peaks.

SUMMARY OF THE INVENTION

The present invention provides methods, compositions, and kits for use in an amplifiable, nonisotopic detection systems. The composition comprises nanocrystals that are functionalized to be water-soluble, and further functionalized to comprise a plurality of polynucleotide strands of a known sequence which extend outwardly from each nanocrystal. While there are several variations of this system, a basic principle of the invention is that a molecular probe is used to detect a target molecule, if present in a sample, by the binding specificity of the molecular probe for the target molecule or a portion thereof; and generation and amplification of a detectable signal by using at least two species of functionalized nanocrystals. A first species of functionalized nanocrystals ("primary dots") have extending therefrom strands of polynucleotides of known sequence, and wherein the primary dots are, or become, operably linked to the molecular probe. A second species of functionalized nanocrystals ("secondary dots") also have strands of polynucleotides of known sequence extending therefrom, wherein the nucleic acid sequence of the polynucleotide strands of the secondary dots is sufficiently complementary to the nucleic acid sequence of the polynucleotide strands on the primary dots such that, under suitable conditions for promoting contact and hybridization, the respective complementary strands hybridize to each other in forming a dendrimer. In multiple steps in which subsequent additions of functionalized nanocrystals alternate between primary dots and secondary dots, a dendrimer of multiple layers of functionalized nanocrystals is formed, thereby resulting in a detectable signal and an exponential increase in the amount of detectable signal that can be detected from a single molecular probe. Additionally provided, are assay kits comprising reagents for the signal amplification system according to the present invention.

The above and other objects, features, and advantages of the present invention will be apparent in the following Detailed Description of the Invention when read in conjunction with the accompanying drawings in which reference numerals denote the same or similar parts throughout the several illustrated views and embodiments.

DETAILED DESCRIPTION OF THE INVENTION

Definitions

Figure 1:
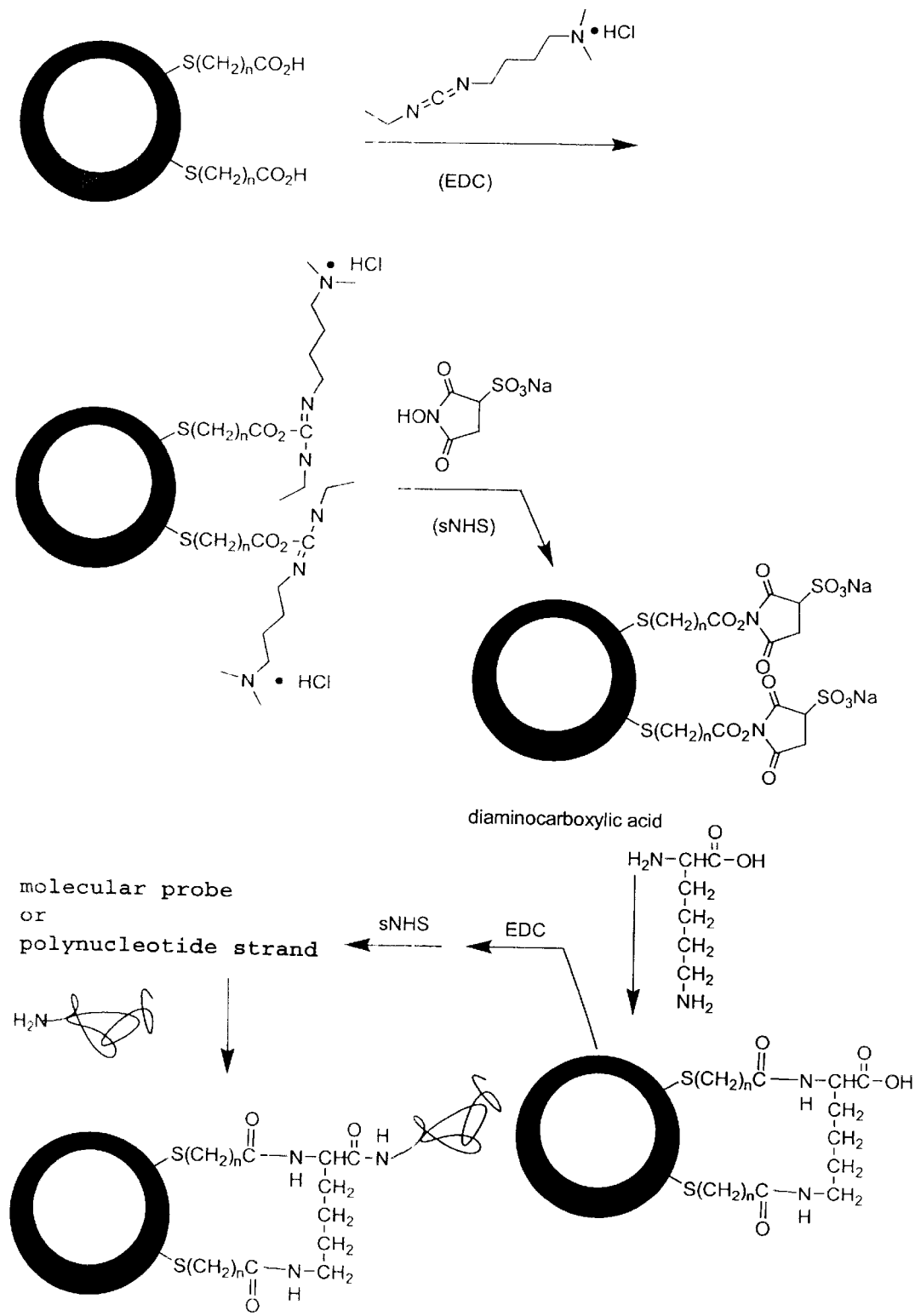
FIG. 1. is a schematic illustrating functionalizing a water-soluble nanocrystal containing a layer of a capping compound to further comprise a coating of a diaminocarboxylic acid, and then operably linking the diaminocarboxylic acid to a molecular probe.

By the term "target molecule" is meant, for the purposes of the specification and claims to refer to a molecule of an organic or inorganic nature, the presence and/or quantity of which is being tested for; and which contains a molecular component (e.g., ligand or sequence or epitope or domain or portion or chemical group or reactive functionality or determinant) for which a molecular probe has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, a substrate, and the like. The target molecule may be in vivo, in vitro, in situ, or ex vivo.

By the term "molecular probe" is meant, for purposes of the specification and claims, to mean a molecule which has binding specificity and avidity for a molecular component of, or associated with, a target molecule. In general, molecular probes are known to those skilled in the art to include, but are not limited to, lectins or fragments (or derivatives) thereof which retain binding function, monoclonal antibodies ("mAb", including chimeric or genetically modified monoclonal antibodies which may be preferable for administration to humans), peptides, aptamers, and nucleic acid molecules (including, but not limited to, single stranded RNA or single-stranded DNA, or single-stranded nucleic acid hybrids, oligonucleotide analogs, backbone modified oligonucleotide analogs, morpholino-based polymers). The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include $F(ab')_2$, Fab', Fab, Fv, scFV, Fd' and Fd fragments. Methods for producing the various fragments or derivatives from mAbs are well known in the art (see, e.g., Plückthum, 1992, *Immunol. Rev.* 130:152–188). For example, $F(ab')_2$ can be produced by pepsin digestion of the monoclonal antibody, and Fab' may be produced by reducing the disulfide bridges of $F(ab')_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. The construction of chimeric antibodies is now a straightforward procedure (Adair, 1992, *Immunological Reviews* 130: 5–40, ) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, *J. Immunol.* 150:2844–2857). Methods for making a chimeric non-human/human mAb in general are described in detail in U.S. Pat. No. 5,736,137. Aptamers can be made using methods described in U.S. Pat. No. 5,789,157. Lectins and fragments thereof are commercially available. Oligonucleotide analogs, backbone modified oligonucleotide analogs, and morpholino-based polymers can be made using methods described in U.S. Pat. Nos. 5,969,135, and 5,596,086, U.S. Pat. Nos. 5.602,240, and 5,034,506, respectively. "Molecular probe" is often used herein, particularly when referring to adding the molecular probe to a sample for detection purposes, or operably linking to a plurality of polynucleotide strands of primary dots, as meaning a plurality of molecules of the molecular probe.

By the term "hybridize" is meant, for purposes of the specification and claims, to refer to a process by which a single-stranded nucleic acid molecule joins with a complementary strand through nucleotide base pairing. As apparent in the art, a sufficient number of complementary base pairs are needed for hybridization, and the selectivity of hybridization depends on the degree of complementarity, the stringency of conditions during the hybridization process, and the length of the hybridizing strands. In a preferred embodiment, nucleic acid molecules, and more particularly polynucleotide strands, which are complementary are hybridizable under "suitable conditions"; i.e., under optimal reaction conditions of temperature, ionic strength, and time of reaction which permit hybridization between the desired complementary nucleic acid molecules and that minimize nondiscriminate hybridization (e.g., disfavor non-homologous base pairing). Typically, such conditions are described ranging from medium stringency to high stringency. Likewise, where a polynucleotide strand lacks sufficient complementarity to specifically hybridize to another polynucleotide strand means that the strands lack sufficient complementarity to hybridize under conditions ranging form medium stringency to high stringency, and more preferably, lack sufficient complementarity to hybridize under conditions ranging from low stringency to high stringency, as understood by those skilled in the art. Also in a preferred embodiment, the two strands which are hybridized are of sufficient complementarity and length that the resulting base paired complex (hybrid) is sufficiently stable to serve the functions of dendrimer formation and detection as described in more detail herein.

By the term "effective amount" is meant, for purposes of the specification and claims and when used in conjunction with a molecule or compound described herein, to refer an amount sufficient to contact and operably link its target for which it has binding specificity (if present in the mixture) for the purposes of signal amplification and detection according to the present invention. For example, an effective amount of secondary dots means that added to a mixture is a sufficient amount of secondary dots to hybridize with primary dots containing complementary polynucleotide strands, if such primary dots are present. In a preferred embodiment, an effective amount comprises an amount that would saturate (e.g., bind substantially all available) any specific and available binding sites of its target (e.g., if a secondary dot, bind to all available primary dots containing complementary polynucleotide strands).

By the term "operably linked" is meant, for purposes of the specification and claims to refer to fusion or bond or an association, of sufficient stability for the purposes of signal amplification and detection according to the present invention, between a combination of different molecules such as, but not limited to, between a linker and a molecular probe, between a molecular probe and the terminal portion of one or more polynucleotide strands of a primary dot; between a linker and a primary dot; between a molecular probe and a primary dot; between a terminal portion of a polynucleotide strand and a coat of the nanocrystal portion of a primary dot; between the quantum dot and a capping compound; between a capping compound and a diaminocarboxylic acid; between a diaminocarboxylic acid and a diaminocarboxylic acid; between a diaminocarboxylic acid and a linker; between a diaminocarboxylic acid and an amino acid; between an amino acid and a molecular probe; between a diaminocarboxylic acid and a polynucleotide strand; and a combination thereof. As known to those skilled in the art, and as will be more apparent by the following embodiments, there are several methods and compositions in which two or more molecules may be operably linked utilizing reactive functionalities. Reactive functionalities include, but are not limited to, bifunctional reagents/linker molecules, biotin, avidin, free chemical groups (e.g., thiol, or carboxyl, hydroxyl, amino, amine, sulfo, etc.), and reactive chemical groups (reactive with free chemical groups).

By the term "linker" is meant, for purposes of the specification and claims to refer to a compound or moiety that acts as a molecular bridge to operably link two different molecules, wherein one portion of the linker is operably linked to a first molecule, and wherein another portion of the linker is operably linked to a second molecule. The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, and the like. The linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. As illustrative examples, to operably link a hydroxyl group of a polynucleotide strand of a primary dot to the amino group of a molecular probe, the linker may have: a carboxyl group to form a bond with the polynucleotide strand, and a carboxyl group to form a bond with the molecular probe; or a carboxyl group to form a bond with the polynucleotide strand, and an aldehyde group to form a bond with the molecular probe; or a carboxyl group to form a bond with the polynucleotide strand, and a halide group to form a bond with the molecular probe. In another example, to operably link a carboxyl group of a polynucleotide strand of a primary dot to the amino group of a molecular probe, the linker can have: an amino group to form a bond with the polynucleotide strand, and a carboxyl group to form a bond with the molecular probe; or an amino group to form a bond with the polynucleotide strand, and a hydroxyl group to form a bond with the molecular probe; or a hydroxyl group to form a bond with the polynucleotide strand, and a sulphonic acid group to form a bond with the molecular probe (see, e.g., U.S. Pat. Nos. 5,792,786, and 5,780,606 for various linkers known in the art). A linker may comprise a primary amine reactive group to react with an amino acid (e.g., lysine) residue of a molecular probe comprising a mAb, and a thiol reactive group to react with a terminally thiolated polynucleotide strand of a primary dot. Heterobifunctional photo-reactive linkers (e.g., phenylazides containing a cleavable disulfide bond) are known in the art. For example, a sulfosuccinimidyl-2-(p-azido salicylamido) ethyl1,3'-dithiopropionate contains a N-hydroxy-succinimidyl group reactive with primary amino groups, and the phenylazide (upon photolysis) reacts with any amino acids. The linker may further comprise a protective group which blocks reactivity with a functional group on the linker which is used to react with and bind to a molecule to be linked. A deprotection reaction may involve contacting the linker to one or more conditions and/or reagents which removes the protective group, thereby exposing the functional group to interact with the molecule to be linked. Depending on the nature of the protective group, deprotection can be achieved by various methods known in the art, including, but not limited to photolysis, acidolysis, hydrolysis, and the like. Depending on such factors as the molecules to be linked, and the conditions in which the method of detection is performed, the linker may vary in length and composition for optimizing such properties as flexibility, stability, and resistance to certain chemical and/or temperature parameters. For example, short linkers of sufficient flexibility include, but are not limited to, linkers having from 2 to 10 carbon atoms (see, e.g., U.S. Pat. No. 5,817,795).

By the term "dendrimer" is meant, for purposes of the specification and claims to refer to a matrix formed by interaction between two or more species of functionalized nanocrystals, wherein the matrix formation is facilitated by the interaction of polynucleotide strands between respective species of functionalized nanocrystals, and wherein a polynucleotide strand becomes held in close association via base pairing and/or covalent crosslinking with a complementary strand.

By the term "strand" is meant, when used in conjunction with or in reference to the term "polynucleotide" and for purposes of the specification and claims to refer to a nucleic acid molecule which is substantially single-stranded (comprising all or a substantial portion of single-strandedness sufficient to hybridize with a complementary single strand in the formation of a dendrimer). There is no particular size, length or content limitations for the strand, so long as it can fulfill its purpose in dendrimer formation as described herein. The nucleic acid composition of the polynucleotides may be selected from molecules which include, but are not limited to, ribonucleotides (RNA), deoxyribonucleotides (DNA), RNA/DNA hybrids, naturally occurring nucleotides, and synthetic or modified nucleotides (e.g., oligonucleotide analogs, backbone modified oligonucleotide analogs, morpholino-based polymers, and the like).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, an amino acid precursor (e.g., citrulline and ornithine are intermediates in the synthesis of arginine), or a combination thereof. In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Additionally, the diaminocarboxylic acid imparts one or more functional advantages to the water-soluble nanocrystal of which it is a part, as will be more apparent from the following embodiments Exemplary diaminocarboxylic acids include, but are not limited to, lysine, asparagine, glutamine, arginine, citrulline, ornithine, 5-hydroxylysine, djenkolic acid, β-cyanoalanine, a synthetic diaminocarboxylic acid (e.g., such as 3,4-diaminobenzoic acid, 2,3-diaminopropionic acid, 2,4-diaminobutyric acid, 2,5-diaminopentanoic acid, 2,6-diaminopimelic acid), and a combination thereof. A diaminocarboxylic acid of the aforementioned diaminocarboxylic acids may be used in a preferred embodiment, and a preferred diaminocarboxylic acid may be used separately in the method according to the present invention to the exclusion of diaminocarboxylic acids other than the preferred diaminocarboxylic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and a combination thereof. An amino γ-aminobutyric acid, and a combination thereof. An amino acid of the aforementioned amino acids may be used in a preferred embodiment, and a preferred amino acid may be used separately in the method according to the present invention to the exclusion of amino acids other than the preferred amino acid.

By the term "capping compound" is meant, for purposes of the specification and claims to refer to a compound having the formula $HS(CH_2)_nX$, wherein X is a carboxylate (carboxylic moiety); or the formula $HS(CH_2)_nYX$, wherein X is a carboxylate and Y is an amine, as will be more apparent from the following descriptions. "n" is a number in the range of from 1 to about 20, and preferably greater than 4. The thiol group of the capping compound forms Cd (or Zn)—S bonds (depending on whether the shell is Cd or Zn), creating a layer which is not easily displaced in solution. Additionally, the carboxylic acid moiety and/or the amine of the capping compound imparts some water solubility to the capped quantum dots. Exemplary capping compounds include, but are not limited to, mercaptocarboxylic acid, or mercaptofunctionalized amines (e.g., aminoethanethiol-HCl, homocysteine, or 1-amino-2-methyl-2-propanethiol-HCl), or a combination thereof. A capping compound of the aforementioned capping compounds may be used in a preferred embodiment, and a preferred capping compound may be used separately in the method according to the present invention to the exclusion of capping compounds other than the preferred capping compound.

By the term "functionalized nanocrystals" is meant, for purposes of the specification and claims to refer to water-soluble nanocrystals comprised of (in order from inner core to outward coatings or layers): a core of CdX wherein X is Se or Te or S; passivated with a shell preferably comprised of YZ wherein Y is Cd or Zn, and Z is S, or Se; coated with a capping compound; and coated with least one additional coating that (a) enhances stability and/or solubility in an aqueous environment; and (b) provides one or more reactive functionalities that may be used to operably link the functionalized nanocrystal to a plurality of polynucleotide strands, or to a linker (one or more linker molecules) which may then be used to operably link the functionalized nanocrystal to a plurality of polynucleotide strands. Thus, a functionalized nanocrystal may further comprise a plurality of polynucleotide strands operably linked thereto. In a preferred embodiment, the at least one additional coat comprises amino acid, wherein each coating of amino acid contains neutral (uncharged) polar functional groups which can hydrogen bond with water, and comprises one or more types of free chemical reactive groups. In a more preferred embodiment, the at least one layer of amino acid that functionalizes the nanocrystal is comprised of a coating of diaminocarboxylic acid. A preferred functionalized nanocrystal may be produced, and used in the method and system according to present invention, to the exclusion of functionalized nanocrystals other than the preferred functionalized nanocrystals The present invention provides compositions which can be used to build three dimensional dendrimers which function to generate and significantly amplify a detectable signal, thereby considerably improving the sensitivity of a non-isotopic detection system. The use of polynucleotide strands to build the dendrimers is fundamental to this invention. Also fundamental to the invention are functionalized nanocrystals which comprise a plurality of polynucleotide strands of a known sequence. In a more preferred embodiment, the plurality of polynucleotide strands are operably linked to the functionalized nanocrystals such that all, or a substantial amount, of one terminal portion of each polynucleotide strand is bound to the functionalized nanocrystal, and wherein the portion of each polynucleotide strand which is not bound to the functionalized nanocrystal extends outwardly from the functionalized nanocrystal, as will be more apparent from the figures and following description.

A basic principle of the method and system for signal amplification using the compositions according to the present invention is that a molecular probe is used to detect a target molecule, if present, by the binding specificity of the molecular probe for the target molecule or a portion thereof; and the molecular probe is, or becomes, operably linked to a primary dot, and successive additions of secondary dots and primary dots result in the formation of a dendrimer, wherein the fluorescence of the primary dots and secondary dots of the dendrimer provide the signal and signal amplification in detecting the binding of the molecular probe to the target molecule. In one embodiment of the present invention, an effective amount of molecular probe is first contacted with a sample under suitable conditions of a reaction for the molecular probe to contact and bind its target molecule, if present, in the sample being analyzed for the presence or absence of the target molecule. Subsequently, an effective amount of primary dots, which have binding specificity for the molecular probe, is added to the reaction. In another embodiment of the present invention, the molecular probe is first operably linked to primary dots, and then an effective amount of the molecular probe-primary dot complex is contacted with the sample under conditions suitable for the molecular probe to contact and bind its target molecule, if present, in the sample being analyzed for the presence or absence of the target molecule. In a further embodiment, the molecular probe is synthesized as a part of the primary dots, and hence, an effective amount of primary dots is contacted with a sample under conditions suitable for the portion comprising the molecular probe to contact and bind its target molecule, if present, in the sample being analyzed for the presence or absence of the target molecule. In this latter embodiment, the molecular probe may be incorporated as a coat which is made part of the nanocrystal portion of the primary dots, or synthesized as part of the polynucleotide stands of the primary dots. Applicable to any of these embodiments, (a) the primary dots are added in an effective amount, and (b) to the primary dots are added, under suitable conditions for contact and hybridization, an effective amount of a species of functionalized nanocrystals ("secondary dots") having polynucleotide strands comprised of sequence complementary to the sequence of the polynucleotide strands of the primary dots (note, that the terms "primary dots" and "secondary dots" are used only for purposes of brevity of description and illustration). Optionally, a wash step may be performed prior to the addition of the secondary dots to the primary dots so as to remove any primary dots in the system that have become non-specifically associated with a target molecule, if present. Under suitable conditions, an effective amount of secondary dots will contact and hybridize (via complementary strands) to the primary dots in forming a dendrimer. In multiple steps in which subsequent additions of an effective amount of functionalized nanocrystals alternate between primary dots and secondary dots, a dendrimer of multiple layers of functionalized nanocrystals is formed, thereby resulting in detectable signal and an exponential increase in the amount of detectable signal for detecting a molecular probe bound to a target molecule.

The compositions according to the present invention comprise quantum dots which are functionalized (a) to be water-soluble, and (b) to further comprise a plurality of polynucleotide strands of a known sequence. Desirable features of the basic quantum dots themselves include that the class of quantum dots can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. The quantum dots typically should have a substantially uniform size of less than 200 Angstroms, and preferably have a substantially uniform size in the range of sizes of from about 1 nm to about 5 nm, or less than 1 nm.

In that regard, quantum dots are preferably comprised of a core of CdX wherein X is Se or Te or S. Such quantum dots are well known in the art. CdX quantum dots can be passivated with an overlayering ("shell") uniformly deposited thereon. A preferred passivating shell is comprised of YZ wherein Y is Cd or Zn, and Z is S, or Se. Quantum dots having a CdX core and a YZ shell have also been generally described in the art. However, a feature of the quantum dots used to operably link to a plurality of polynucleotide strands is that the quantum dots have been functionalized to be water-soluble nanocrystals. "Water-soluble" is used herein to mean that the nanocrystals are sufficiently soluble or suspendable in a aqueous-based solution including, but not limited to, water, water-based solutions, buffer solutions, that are used in detection processes, as known by those skilled in the diagnostic art.

Figure 2A:
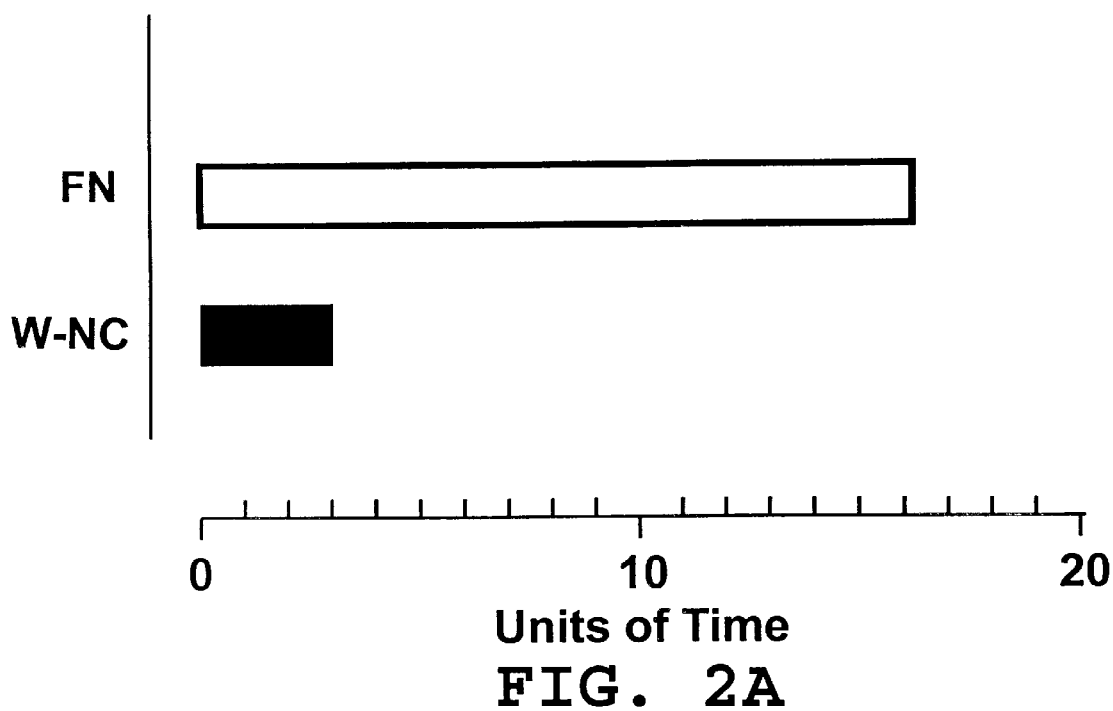
FIG. 2A is a bar graph comparing the stability of capped quantum dots ("W-SN") to the stability of functionalized nanocrystals ("FN") under oxidizing conditions.
Figure 2B:
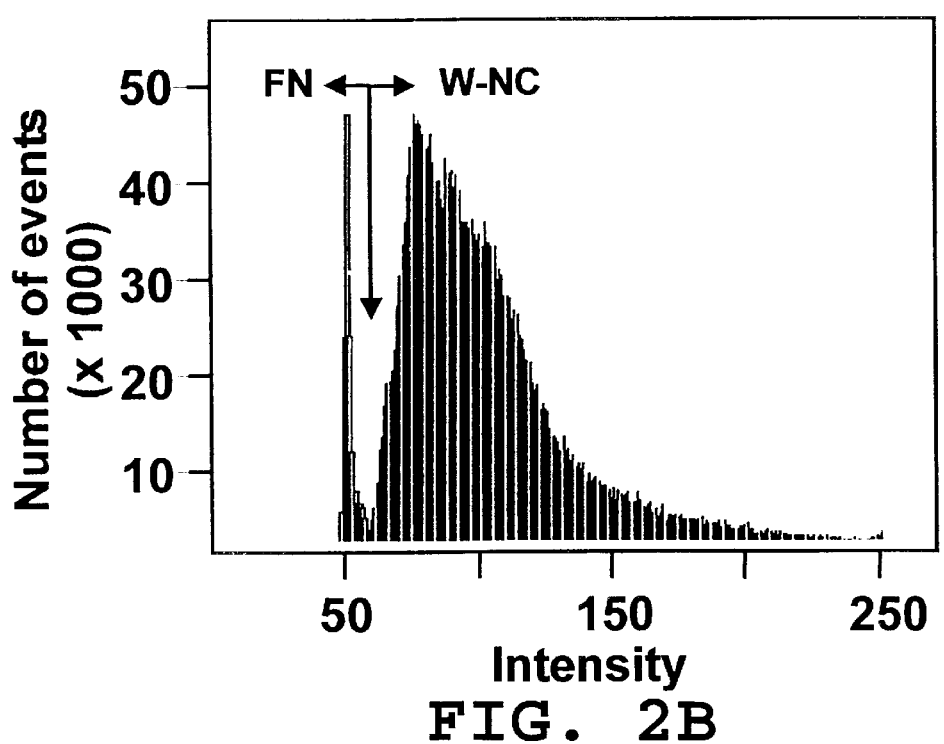
FIG. 2B is a bar graph comparing the non-specific binding of capped quantum dots ("W-SN") to the non-specific binding of functionalized nanocrystals ("FN").

Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with one which will make the quantum dots water-soluble. For example, a mercapto-carboxylic acid is used to exchange with the trialkylphosphine oxide. Exchange of the capping group is accomplished by treating the water-insoluble quantum dots with a large excess of mercaptocarboxylic acid, either neat (e.g., at 60° C.) or in $CHCl_3$ solution (Chen and Nie, 1998, *Science* 281:2016–2018), followed by extraction into water. The mercaptocarboxylic acid coating imparts some water solubility to the quantum dots, whereas quantum dots capped with trialkylphosphine oxide are soluble only in organic, non-polar (or weakly polar) solvents. Another method to make the CdX core/YZ shell quantum dots water-soluble is by the formation of a layer of silica around the dots (Bruchez et al., 1998, *Science* 281:2013–2015). An extensively polymerized polysilane shell imparts water solubility to nanocrystalline materials, as well as allowing further chemical modifications of the silica surface. However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the quantum dots, thereby exposing the surface of the quantum dots in resulting in "destabilized quantum dots". Destabilized quantum dots form aggregates when they interact together, and the formation of such aggregates eventually leads to irreversible flocculation of the quantum dots. Additionally, carboxylate groups can cause non-specific binding, particularly to one or more molecules in a sample other than the target molecule, which is not desirable in a detection assay. Described herein are quantum dots consisting essentially of a core of CdX wherein X is Se or Te or S; the core is then passivated with a shell preferably comprised of YZ wherein Y is Cd or Zn, and Z is S, or Se; and the shell is overlayed with a capping compound. However, it has been discovered that such quantum dots have disadvantages, as will be more apparent from the following descriptions (see also, FIGS. 2A and 2B). Hence, in a preferred embodiment of the present invention, provided are functionalized nanocrystals comprising a plurality of polynucleotide strands to provide signal and signal amplification, and assay kits therefor.

EXAMPLE 1

In this embodiment is illustrated the production of exemplary, basic quantum dots appropriate for functionalization according to the present invention. The quantum dots comprise a CdSe core, and a ZnS shell, "(CdSe)ZnS", and a layer of capping compound. TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 µl, 0.1 mmol) and 1 M trioctylphosphine-Se solution (90 µl, 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of quantum dots over time, by the observation of the absorption spectra. The temperature may be changed, or the reaction halted, upon reaching quantum dots of the desired characteristics. For example, the reaction vessel was cooled to about 60° C., 40 ml of methanol was added to cause the quantum dots to flocculate. After centrifugation, a brightly colored liquid layer of quantum dots dissolved in trioctylphosphine remained. The methanol/TOPO layer was decanted off, and pyridine (10 ml) was added to the solution of quantum dots and allowed to stand for at least one hour. The quantum dots were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS quantum dots, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The passivated quantum dots were stored in this solution to ensure that the surface of the quantum dots remained passivated with pyridine.

To cap the quantum dots, the pyridine overcoating of the (CdX) core/YZ shell quantum dots were exchanged with a capping compound which contributes to the water-solubility of the capped quantum dots. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. Overnight incubations are ideal. Chloroform is added to precipitate the quantum dots and wash away excess thiol. The quantum dots were isolated by centrifugation, washed once more with chloroform, and then washed with hexanes. The residue was briefly dried with a stream of argon. The resultant quantum dots were resuspended in an aqueous solution, centrifuged once more, filtered through a 0.2 µm filter, degassed with argon, and stored in an amber vial. As mentioned previously, oxidation may result in the capping compound becoming destabilized; and destabilization can result in irreversible flocculation of the capped quantum dots.

EXAMPLE 2

Illustrated in this Example is a preferred embodiment of exemplary functionalized nanocrystals. Capped CdX core/YZ shell quantum dots were produced using the methods illustrated in Example 1. The capped quantum dots were functionalized by a the addition of a coating by operably linking organic molecules comprising a diaminocarboxylic acid to the capping compound in forming functionalized nanocrystal. In a preferred embodiment, the diaminocarboxylic acid (a) contributes to the water-solubility of the functionalized nanocrystal because it has polar functional groups which can hydrogen-bond with water; (b) has at least two free functional groups which are carboxyl-reactive, thereby enabling the diaminocarboxylic acid molecule to operably link to, and may crosslink, carboxyl groups extending from the capping compound on the capped quantum dots; (c) once operably linked to the capping compound, has one or more free functional groups which can be used for operably linking to one or more polynucleotide strands (or to a linker); and (d) provides other beneficial properties to the resultant functionalized nanocrystals. A preferred diaminocarboxylic acid comprises lysine. For example, and as illustrated in FIG. 1, mercaptoacetic acid-capped quantum dots were dissolved in an aqueous buffer system (pH of about 7). The buffer may comprise such buffers as PBS or HEPES; however, the presence of phosphate may dramatically decrease the lifetime of the cross-linking agent. To the capped quantum dots was added EDC (1-ethyl-3-[3-dimethyl-aminopropyl] carbdiimide) and sulfoNHS (sulfo-N-hydroxy-succinimide) in 500–1000 times excess. The resulting solution was stirred at room temperature for 30 minutes. Mercaptoethanol was added to neutralize unreacted EDC at 20 mM concentration, followed by stirring for 15 minutes. The entire solution was then added dropwise, with stirring, to a solution of lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice.

Figure 3:
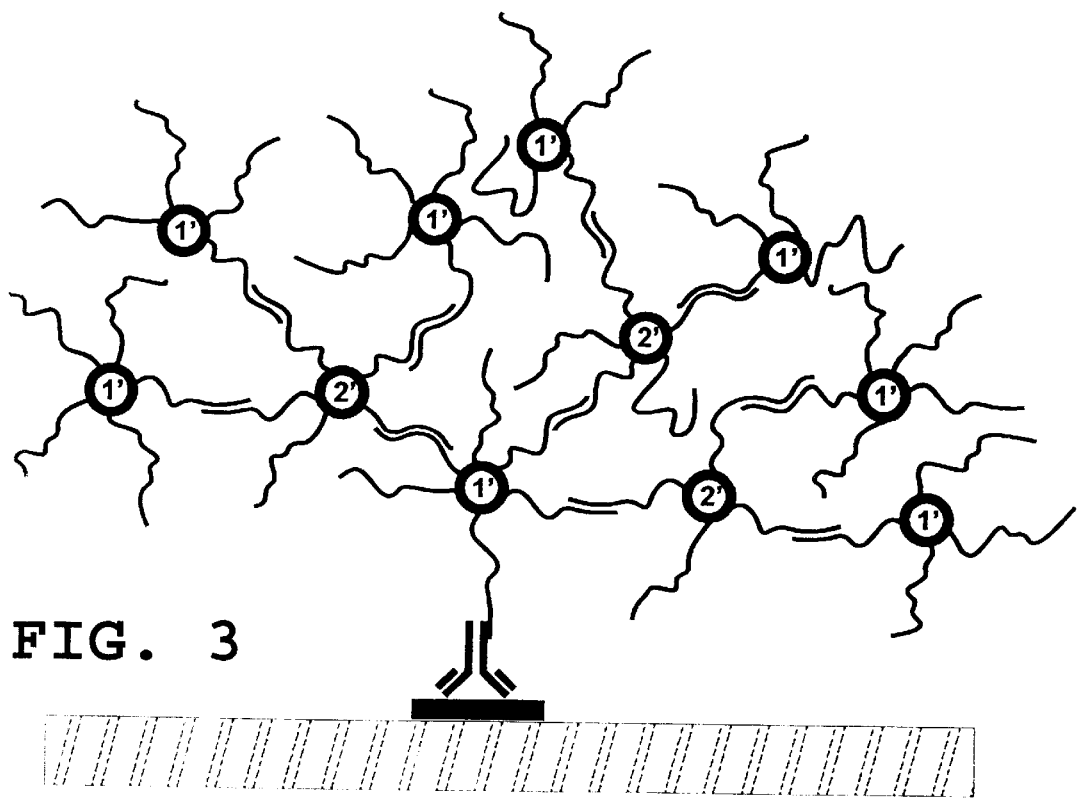
FIG. 3 is a schematic illustration showing a functionalized nanocrystal comprising a primary dot which is operably linked to a molecular probe comprising an antibody (which is shown here as bound to its target molecule); and showing dendrimer formation resulting from subsequent and successive additions of secondary dots and primary dots

Regarding stability, as shown in FIG. 2, the functionalized nanocrystals containing a coat of diaminocarboxylic acid ("FN") unexpectedly show a significant increase in stability in an aqueous environment compared to quantum dots having an outer layer of just the capping compound ("W-SN), when exposed over time to identical conditions of an oxidizing environment (e.g., light and air). Additionally, as shown in FIG. 3, functionalized nanocrystals containing a coat of diaminocarboxylic acid ("FN") unexpectedly result in a significant decrease in non-specific binding compared to quantum dots having an outer layer of just the capping compound ("W-SN), when each were contacted with a surface that is both hydrophilic and hydrophobic (e.g., as may be encountered in a detection system), followed by washing of the surface, followed by detection of residual nanocrystals (as measured by number of events of fluorescence versus the intensity of fluorescence; using a fluorescence microscope with a video camera attachment, time of exposure- $\frac{1}{30}^{th}$ of a second).

In another embodiment, as also illustrated in FIG. 1, the coating comprising diaminocarboxylic acid of the functionalized nanocrystals is then operably linked to a plurality of polynucleotide strands; or to a combination comprising a linker which is then operably linked to the molecular probe, and a plurality of polynucleotide strands. For example, depending on factors such as the species of diaminocarboxylic acid and/or the amount of diaminocarboxylic acid which is used to operably link to the capping compound, each operably linked diaminocarboxylic acid may have one or more reactive functionalities (e.g., free amino group, free carboxyl group, and a combination thereof) that can be used to operably link to a reactive functionality of a polynucleotide strand (or to a linker). As an illustrative example, polynucleotide strands having free carboxyl-reactive groups (e.g., amine groups) can be operably linked to free carboxyl groups of the molecules of diaminocarboxylic acid comprising a coating of the functionalized nanocrystals using methods known in the art (e.g., treatment with EDC, followed by treatment with sulfo-NHS, as previously described herein). In an alternative, polynucleotide strands having free amino-reactive groups (e.g., carboxyl groups) can be operably linked to free amino groups of the molecules of diaminocarboxylic acid comprising a coating of the functionalized nanocrystals using methods known in the art. If desirable, essentially the same procedure can be used to operably link an additional amino acid layer onto the diaminocarboxylic acid layer, and then to operably link the resultant functionalized nanocrystal to a plurality of polynucleotide strands (or linker).

To illustrate this embodiment, molecules representative of polynucleotide strands having free carboxyl-reactive groups (amine groups) were operably linked to the functionalized nanocrystals using the methods summarized herein. Briefly, functionalized nanocrystals (1 ml, $8.1 \times 10^{-9}$ mol) were esterified by treatment with EDC ($8.1 \times 10^{-6}$ mol), followed by treatment with sulfo-NHS ($8.9 \times 10^{-6}$ mol) at ambient temperature in buffered aqueous solution (at about pH 7.4) for 30 minutes. 2-mercaptoethanol was added to the solution at a concentration of 20 mM, and the mixture was stirred for 15 minutes to quench any unreacted EDC. The nanocrystals were then contacted with a mol concentration of molecules (depending on the size, and desired number) for operably linking a plurality of the molecules to the functionalized nanocrystals, and the reaction mixture was stirred for 2 hours (e.g., or reacted in other suitable conditions for forming an amide bond between the EDC-activated carboxylates of the diaminocarboxylic acid layer and the amine groups on the polynucleotide strands). Ethanolamine was added at a concentration of 30 mM to quench the coupling reaction, and the reaction mixture was stirred for 30 minutes. The resulting solution was then filtered to remove excess reagents. The concentrated material was then diluted to 1 ml in buffer (e.g., PBS) or other suitable aqueous solution.

EXAMPLE 3

This Example illustrates additional embodiments comprising functionalized nanocrystals comprising a plurality of polynucleotide strands. The polynucleotide strand is a nucleic acid molecule which is totally or substantially single-stranded and has no particular size, length or content limitations, so long as the polynucleotide strand can fulfill its purpose in dendrimer formation. The nucleic acid composition of the polynucleotides may be selected from molecules which include, but are not limited to, ribonucleotides (RNA), deoxyribonucleotides (DNA), RNA/DNA hybrids, naturally occurring nucleotides, and synthetic or modified nucleotides (e.g., oligonucleotide analogs, backbone modified oligonucleotide analogs, and morpholino-based polymers). A preferred length of the polynucleotide strand is determined from such factors as the nucleic acid composition (nucleobase type; e.g., analog or naturally occurring), the desired specificity of annealing to its complementary strand, the sequence of nucleobases, and desired annealing temperatures. In a preferred embodiment, the length of the polynucleotide strand is a number of nucleobases wherein the number is between about 6 and about 50. In a more preferred embodiment, the length of the polynucleotide strand is a number of nucleobases wherein the number is between about 10 and about 20. As shown in SEQ ID Nos: 1–4, a preferred length is about 18 nucleobases. The content requirement for the polynucleotide strand is that it be comprised of a known nucleotide sequence. Thus, functionalized nanocrystals have extending therefrom a plurality of polynucleotide strands of a known sequence It is apparent to those skilled in the art that the polynucleotide strand may be comprised of a plurality of a single, repeated nucleobase; or a plurality a combination of nucleobases. For example, such a sequence can be made up of a combination of nucleobases (e.g., of more than one type of nucleobase, wherein the nucleobase types comprise A, T, C, G, and U). However, in a preferred embodiment, the known sequence substantially comprises (about 60% to about 100%) of a single type of nucleobase. In illustrating this preferred embodiment, SEQ ID NO:1 is a polynucleotide strand sequence substantially comprised of A; SEQ ID NO:2 is a polynucleotide strand sequence substantially comprised of T; SEQ ID NO:3 is a polynucleotide strand sequence substantially comprised of G; and SEQ ID NO:4 is a polynucleotide strand sequence substantially comprised of C. Formation of dendrimers requires that a species of functionalized nanocrystals comprising a plurality of polynucleotide strands ("primary dots") have polynucleotide strands comprised of a known sequence that are complementary in sequence to the polynucleotide strands of another species of functionalized nanocrystals ("secondary dots"). For purposes of illustration, but not limitation, a primary dot comprises a plurality of polynucleotide strands, each strand substantially comprising polyA (e.g., SEQ ID NO:1); and a secondary dot comprises a plurality of polynucleotide strands, each strand substantially comprising polyT (e.g., SEQ ID NO:2). In another nonlimiting illustration, a primary dot comprises a plurality of polynucleotide strands, each strand substantially comprising AG repeats (e.g., SEQ ID NO:5); and a secondary dot comprises a plurality of polynucleotide strands, each strand substantially comprising TC repeats (e.g., SEQ ID NO:6).

In addition to the preferred embodiment illustrated in Example 2 herein, using techniques known in the art, a plurality of polynucleotide strands may be operably linked to functionalized nanocrystals in forming functionalized nanocrystals comprising a plurality of polyunucleotide strands according to the present invention. Preferably, each polynucleotide strand is operably linked to the functionalized nanocrystal such that contact is substantially between a single terminus of the polynucleotide strand and a coating of the functionalized nanocrystal. Such arrangement provides for the polynucleotide extending outwardly from the resultant functionalized quantum dot, optimally allows for a plurality of polynucleotide strands to be attached to the functionalized nanocrystal, and may provide a minimum of quenching of light emission when such fluorescence emission is emitted by an excited functionalized nanocrystal. To operably link each polynucleotide strand to a functionalized nanocrystal, utilized is one or more reactive functionalities.

In another preferred embodiment, carboxylate-terminated capped quantum dots are produced, such as by the method illustrated in Example 1 herein, or a similar method. The carboxylate groups of the capping compound and a carboxyl-reactive group of a linker are reacted by a means which catalyzes the formation of a chemical association or bond formation between the carboxylate groups and the carboxyl-reactive groups. As an example, using methods similar to that illustrated in Example 2 herein, EDC was used to operably link a linker comprising a molecule having binding specificity for biotin to capped quantum dots in forming functionalized nanocrystals. Molecules having binding specificity for biotin are known in the art to include, but are not limited to, avidin, streptavidin, and derivatives or modified versions thereof; e.g., neutravidin, nitro-avidin, nitro-streptavidin, aceylated avidin, and the like. For purposes of brevity of description, but not limitation, a linker having biotin-binding specificity will be referred to hereinafter as "avidin". In an illustrative embodiment, quantum dots capped by a coating with 11-mercaptoundecanoic acid, and deprotonating with potassium-t-butoxide. The carboxylated quantum dots were then esterified by treatment with EDC followed by sulfo-N-hydroxy-succinimide (sNHS). These quantum dots were then contacted with avidin under sufficient conditions to form an amide bond between the EDC-activated carboxylate of the capped quantum dot and the amine groups on avidin; thereby forming functionalized nanocrystals that were avidinylated. The avidinylated, functionalized nanocrystals may then be contacted with and operably linked to a plurality of polynucleotide strands, each of which contains one or more biotin molecules (comprising native biotin, or a biotin derivative having avidin-binding activity; e.g., biotin dimers, biotin multimers, carbo-biotin, and the like). Preferably, each of the plurality of polynucleotide strands are biotinylated at a single terminus of the polynucleotide strand. Using methods known to those skilled in the art, biotin molecules can be added to or incorporated in a polynucleotide strand, and even localized to one terminus, such as by directing synthesis of the polynucleotide strands with nucleotides and biotin-nucleotides, or by biotinylating the 5' aminogroup of the polynucleotide with sulfo-NHS-biotin. Thus, by contacting avidinylated, water-soluble quantum dots with biotinylated polynucleotide strands, formed is a functionalized nanocrystal comprising a plurality of polynucleotide strands extending therefrom.

In another preferred embodiment, the functionalized nanocrystals of the present invention are produced using reactive functionalities comprising thiol group and thiol reactive groups. One illustration of this embodiment involves use of maleimide derivatives. For example, CdX core/YZ shell quantum dots are capped by a coating with mercapto-functionalized amines (e.g., aminoethanethiol-HCl, homocysteine, or 1-amino-2-methyl-2-propanethiol-HCl). Thus, the cap comprises reactive functionalities comprising amine groups. To these capped quantum dots are added (either in the presence or absence of EDC) a maleimide derivative that reacts with the free amine groups. Such a maleimide derivative may include, but is not limited to 3-maleimidopropionic acid N-hydroxy-succinimide ester, 3-maleimidopropionic acid, 3-maleimido-benzoic acid N-hydroxy-succinimide ester, 4-(maleimido-methyl)-1-cyclohexanecarboxylic acid N-hydroxy-succinimide ester. The resultant functionalized nanocrystals, having thiol-reactive groups, can interact with and bind to a plurality of polynucleotide strands, wherein each polynucleotide strand has been previously derivatized with one or more thiol groups, using methods known in the art for operably linking a thiol group to a thiol-reactive group. Generally, it is preferred that the polynucleotide strand be derivatized substantially at either its 3' or 5' terminus ("capped") with the thiol group. Exemplary means for capping one or more thiol groups to nucleotides are known in the art (see, e.g., U.S. Pat. Nos. 5,811,534, 5,663,242, 5,441,867, and 5,412,087, the disclosures of which are herein incorporated by reference). Thus, formed are functionalized nanocrystals comprising a plurality of polynucleotide strands extending therefrom.

In another preferred embodiment, the functionalized nanocrystals of the present invention are produced utilizing reactive functionalities comprising amine groups and amine reactive groups. One illustration of this embodiment involves capping CdX core/YZ shell quantum dots with a coating comprising mercapto-functionalized amines (e.g., aminoethanethiol-HCl, homocysteine, or 1-amino-2-methyl-2-propanethiol-HCl). Thus, the cap comprises reactive functionalities with amine groups. These capped quantum dots are contacted, and operably linked, to a plurality of polynucleotide strands, wherein each polynucleotide strand has been previously derivatized with one or more amino reactive groups. Amino reactive groups are known to those skilled in the art to include, but are not limited to, active ester groups, haloacetyl groups, azide groups, isocyanate groups, isothiocyanate groups, and acid anhydride groups (see, e.g., U.S. Pat. No. 5,580,923, the disclosure of which is herein incorporated by reference). Exemplary means for capping one or more amino reactive groups to nucleotides are known in the art previously (e.g., attachment of an ester to the 3' or 5' terminus of an oligonucleotide, U.S. Pat. No. 5,639,604; attachment of an aryl azide, U.S. Pat. No. 5,700,921; the disclosures of which are herein incorporated by reference).

EXAMPLE 4

This example illustrates various embodiments of using functionalized nanocrystals comprising a plurality of polynucleotide strands extending therefrom in a method of detection of a target molecule using the signal generation and signal amplification afforded by the dendrimer formation according to the present invention. In a preferred embodiment, functionalized nanocrystals having extended therefrom a plurality of polynucleotide strands of a known sequence comprise primary dots, and to each primary dot is operably linked to a molecular probe. As apparent to one skilled in the art from the descriptions herein, the operably linking of the primary dot to the molecular probe can be done in a manner selected from the group consisting of prior to the addition of the molecular probe to a sample being analyzed for a target molecule, after the molecular probe has been added to the sample being analyzed for a target molecule, and a combination thereof. As previously described in more detail herein, the molecular probe may be any probe used in a detection system to detect the presence or absence of a desired target molecule for which the molecular probe has binding specificity and avidity.

In one illustrative embodiment, and as shown in FIG. 3, the molecular probe may be a mAb. In one variation of this embodiment, the primary dots are first reacted with, and operably linked to, molecular probe prior to the addition of an effective amount of the primary dot-molecular probe complex to a sample being analyzed for the presence or absence of a target molecule. In another illustrative embodiment, and in a detection system, molecular probe is first added in an effective amount to a sample being analyzed for the presence or absence of a target molecule in suitable conditions for the molecular probe to contact and bind to target molecule if present in the sample. Optionally, a wash step may be performed to remove from the detection system any unbound or nonspecifically bound molecular probe. Primary dots are added in an effective amount to contact and operably link with molecular probe that may be present in the detection system. In either of these illustrative embodiments, the terminal portions of the polynucleotide strands that are not bound to the primary dots, and that extend outwardly from the functionalized nanocrystal ("free ends") comprise one or more reactive functionalities (e.g., a linker) that may be used to contact and operably link to one or more reactive functionalities associated with the mAb. For example, as previously described herein and using methods known to those skilled in the art, biotin molecules can be added to or incorporated in a polynucleotide strand so as to be localized to one terminus (e.g., by incorporating biotin-deoxynucleotides during synthesis, or by biotinylating the 5' aminogroup of the polynucleotide with sulfo-NHS-biotin). An mAb (or other molecular probe comprising a protein such an antibody molecule, lectin, and the like) may be attached (conjugated, coupled, etc.) to avidin using methods known to those skilled in the art. Such attachment should take place in a portion of the molecular probe which does not substantially affect the binding of the molecular probe to its ligand. For example, mAb and avidin may be conjugated with a thio-ether linkage using methods known in the art. Thus, the free ends of the polynucleotide strands comprising biotin are contacted with and operably linked to the avidinylated mAb in operably linking the functionalized naocrystals to the molecular probes. This biotin-avidin system may be used to either operably link the primary dots with molecular probe prior to the addition of the molecular probe to a sample being analyzed for the presence or absence of a target molecule; or to operably link the primary dots to the molecular probe after the molecular probe has already been added to the sample being analyzed; or a combination thereof. As shown in FIG. 3, after the molecular probe and primary dot (1') have been added, successive additions of secondary dots (2') (having polynucleotide strands complementary in sequence to the polynucleotide strands of the primary dots) and primary dots may be added to form dendrimers.

Figure 4A:
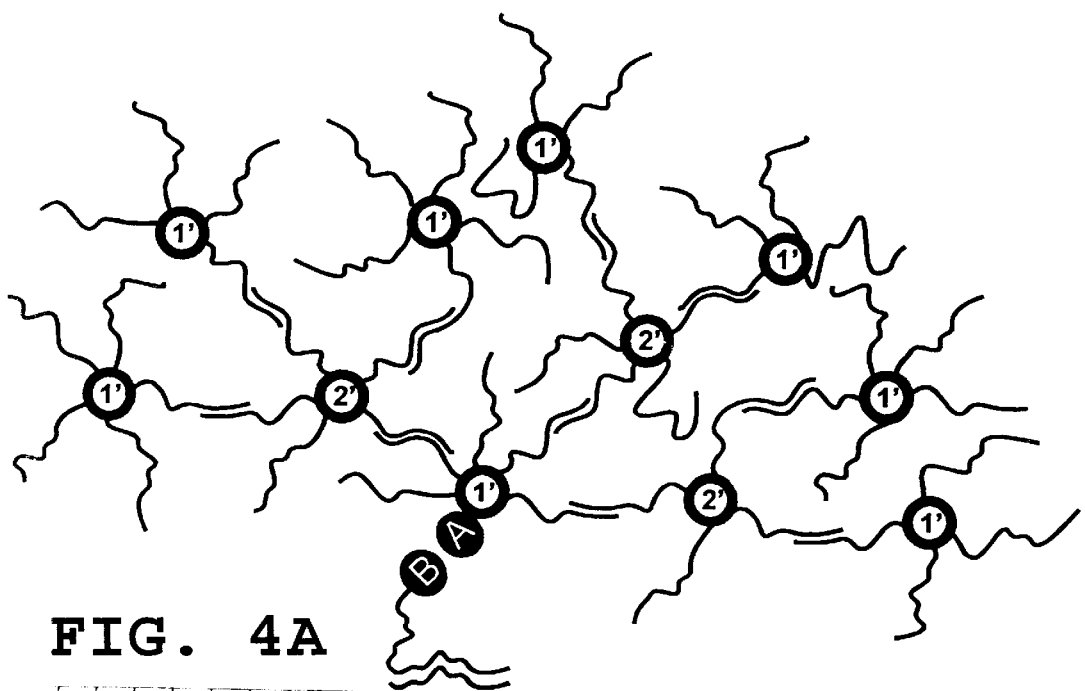
FIG. 4A is a schematic illustration showing an avidinylated functionalized nanocrystal comprising a primary dot operably linked to a molecular probe comprising a biotinylated oligonucleotide (which is shown here as bound to its target molecule); and showing dendrimer formation resulting from subsequent and successive additions of secondary dots and primary dots.
Figure 4B:
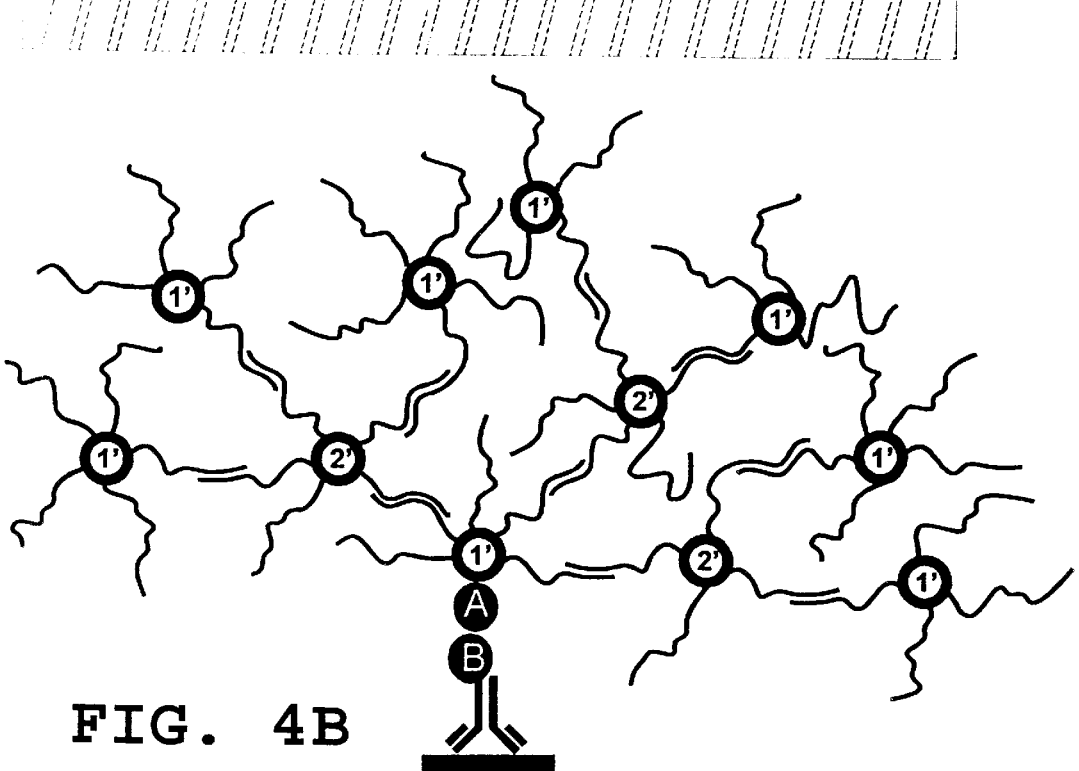
FIG. 4B is a schematic illustration showing an avidinylated functionalized nanocrystal comprising a primary dot which is operably linked to a molecular probe comprising a biotinylated antibody (which is shown here as bound to its target molecule); and showing dendrimer formation resulting from subsequent and successive additions of secondary dots and primary dots.

In another illustrative embodiment, and as illustrated in FIGS. 4A and 4B, the functionalized nanocrystals comprising a plurality of polynucleotide strands are operably linked to the molecular probe via one or more reactive functionalities, wherein the operably linking takes place between a coating of the functionalized nanocrystals (other than the polynucleotide strands) and the molecular probe. For example, as previously described herein in more detail, functionalized nanocrystals may be avidinylated, and then reacted in a controlled manner so as to operably link a finite number of a plurality of biotinylated polynucleotide strands (e.g., by limiting the ratio of polynucleotide strands:functionalized nanocrystals in the reaction for producing functionalized nanocrystals comprising a plurality of polynucleotide strands). Generally, each avidin molecule can bind up to 4 biotin molecules. Thus, by limiting the number of biotinylated polynucleotide strands operably linked thereto, a functionalized nanocrystal may still have avidin capable of binding one or more biotin molecules, such as may be present on a molecular probe. Therefore, using methods known to those skilled in the art, the molecular probe may be biotinylated. Biotinylation of oligonucleotides has been previously described herein. Biotinylated molecular probes comprising proteins (e.g., lectins, mAbs, etc.) are commercially available, or can be produced by one of several methods known in the art such as derivatization of the protein via lysine e-amino groups, or via thiol groups generated by reduction of cysteines. Thus, as illustrated in FIG. 4A (illustrating a molecular probe comprising a biotinylated ("B") nucleic acid molecule; e.g., an oligo probe) and in FIG. 4B (illustrating a molecular probe comprising a biotinylated ("B") antibody), an avidin ("A") of the primary dots (1') is contacted with and operably linked to the biotinylated ("B") molecular probe. This biotin-avidin system may be used to either operably link the primary dot with molecular probe prior to the addition of the molecular probe to a sample being analyzed for the presence or absence of a target molecule, or to operably link the primary dot to the molecular probe after the molecular probe has already been added to the sample being analyzed. As shown in FIGS. 4A and 4B, after the molecular probe and primary dot (1') have been added, successive additions of secondary dots (2') (having polynucleotide strands complementary in sequence to the polynucleotide strands of the primary dots) and primary dots may be added to form a dendrimer.

In another illustrative embodiment, and using the methods illustrated above, free ends of polynucleotide strands may comprise one or more reactive functionalities used to operably link molecular probe. In this embodiment, preferably the primary dots are operably linked to the molecular probe prior to the addition of the molecular probe to the sample being analyzed for the presence or absence of target molecule. For example, and as previously described in more detail herein, a terminal portion of a polynucleotide strand may be capped with one or more thiol groups. A molecular probe may be derivatized to contain one or thiol-reactive groups using methods known to those skilled in the art (e.g., using a hetero-bifunctional crosslinking reagent such as SMCC- succinimidyl 4-(N-maleimidomethyl)cyclohexane-1-carboxylate; or SPDP- succinimidyl 3-(2-pyridyldithio) propionate). Under suitable conditions, contacting the thiol groups contained on the free ends of the polynucleotide strands with the thiol-reactive groups may result in operably linking the primary dots to the molecular probes. The resultant primary dot-molecular probe complex may then be added to the sample. Successive additions of secondary dots and primary dots may then be added in forming dendrimers if target molecule is present. Alternately, and similarly as described above, the quantum dots are capped with mercapto-functionalized amines; the capped quantum dots are functionalized by the addition of a maleimide derivative that reacts with amino groups of the capping compound; the functionalized nanocrystals are operably linked to thiol-derivatized polynucleotide strands in a controlled manner so as to bind a finite number of a plurality of thiolated polynucleotide strands; and the remaining free thiol-reactive groups operably link to thiolated molecular probe in forming thio-ether bonds between the primary dots and molecular probe. A molecular probe, such as one comprised of protein (e.g., antibody, lectins, peptides, and the like) may be derivatized to contain thiol groups using methods known to those skilled in the art. For example, a thiol group may be generated by a partial reduction of the protein. Thus, the primary dot comprises a plurality of polynucleotide strands, and further comprises one or more molecules of molecular probe. The resultant primary dots may then be added to a sample being analyzed for the presence or absence of a target molecule, followed by successive additions of secondary dots and primary dots. The primary dots added in the successive additions may have or lack molecular probe operably linked thereto.

Figure 5:
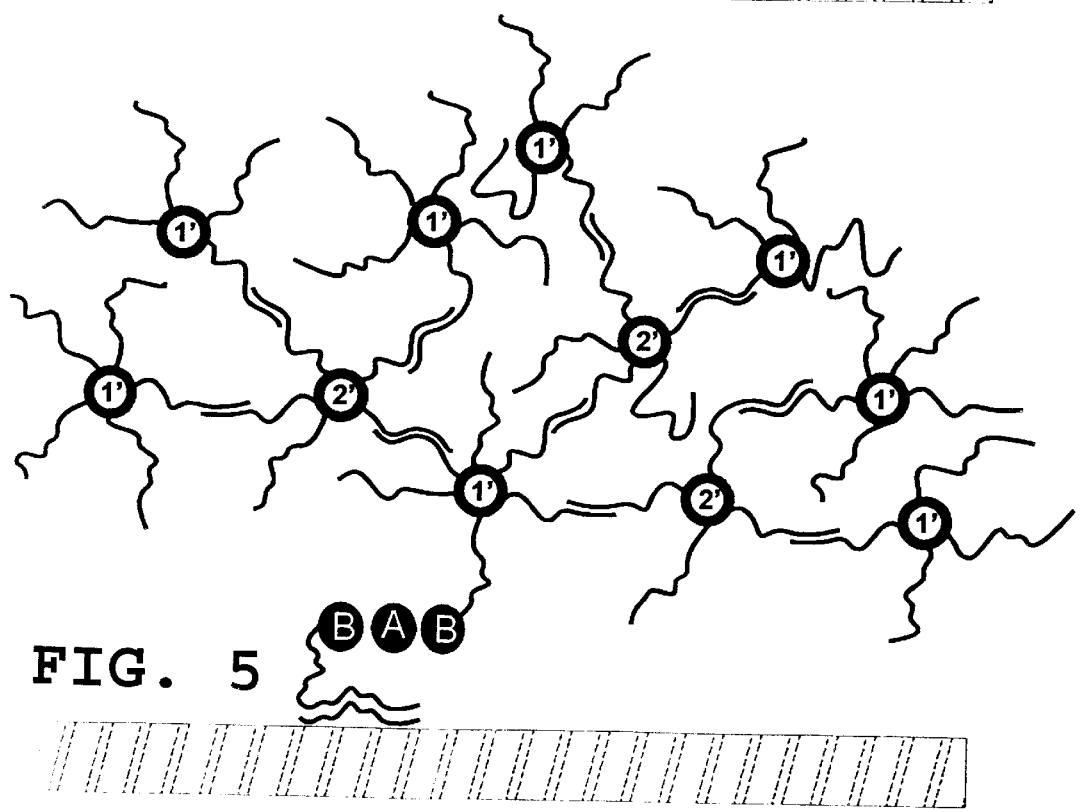
FIG. 5 is a schematic illustration showing an avidin intermediate which is used to operably link biotinylated polynucleotide strands of a functionalized nanocrystal comprising a primary dot to a biotinylated molecular probe (which is shown here as bound to its target molecule); and showing dendrimer formation resulting from subsequent and successive additions of secondary dots and primary dots.

In another illustrative embodiment, and as shown in FIG. 5, a linker may be used to contact and operably link a polynucleotide strand of the primary dot to a molecular probe. For example, as previously described herein and using methods known to those skilled in the art, biotin molecules can be added to or incorporated in a polynucleotide strand so as to be localized to the free end of the polynucleotide strand. Likewise, a molecular probe can be biotinylated (e.g., a biotinylated oligonucleotide probe, a biotinylated mAb, etc.). As illustrated in FIG. 5, avidin ("A") is used as a linker to operably link the biotinylated ("B") polynucleotide strands of primary dots to biotinylated ("B") molecular probe, as generally, avidin can bind multiple molecules of biotin. It will be apparent to those skilled in the art that there are several ways in which avidin may be used as a linker. For example, the avidin may be first added to the molecular probe (either in the sample, or before added to the sample), and then the primary dots are added; or the avidin may be first added to the primary dots before adding the primary dots to the molecular probe; or the avidin may be added simultaneous with the mixture of the primary dots with the molecular probe. In embodiments in which the avidin is first added to either of the primary dots or the molecular probe, a wash step may be performed to remove any unbound avidin before the next component is added. As shown in FIG. 5, after addition of the biotinylated ("B") primary dots (1'), avidin ("A"), and the biotinylated ("B") molecular probe, successive additions may be made of secondary dots (2') and primary dots (1').

Figure 6A:
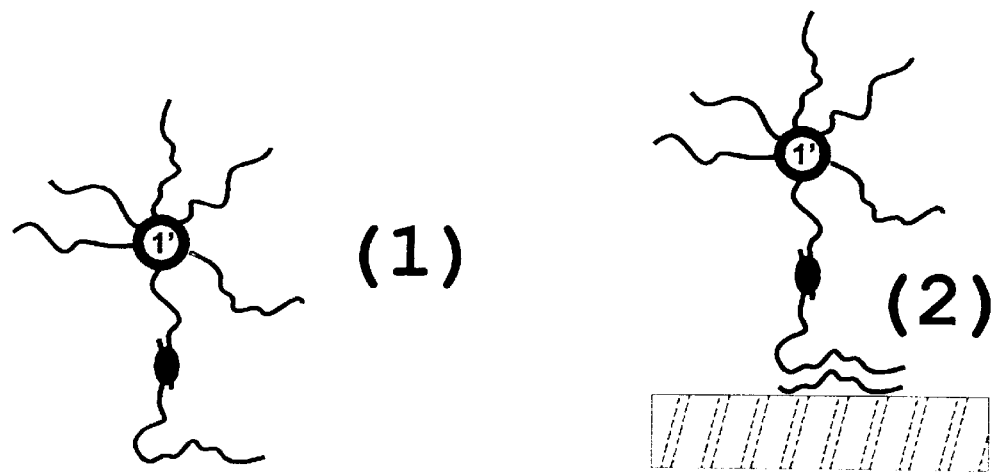
FIG. 6A is a schematic illustration showing use of a linker to operably link a polynucleotide strand of a functionalized nanocrystal to a molecular probe (step 1), and subsequent interaction of the molecular probe with its target molecule (step 2).
Figure 6B:
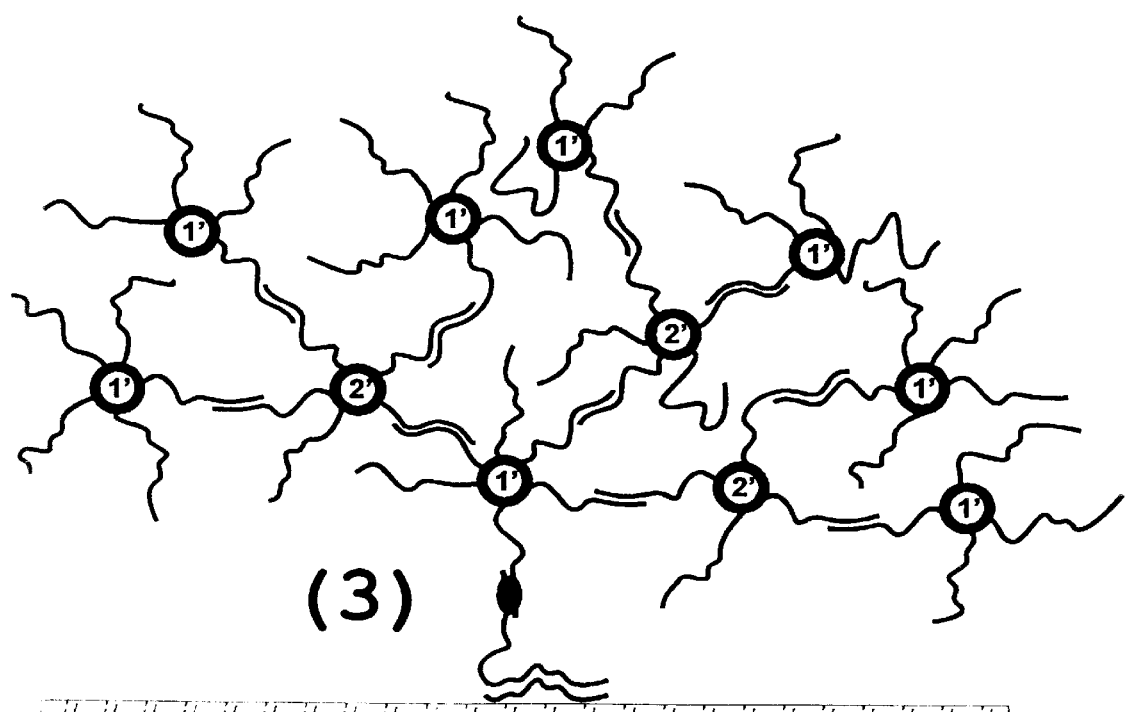
FIG. 6B is a schematic illustration showing a process (step 3) continued from FIG. 6A, wherein subsequent and successive additions of secondary dots and primary dots result in dendrimer formation.
Figure 7:
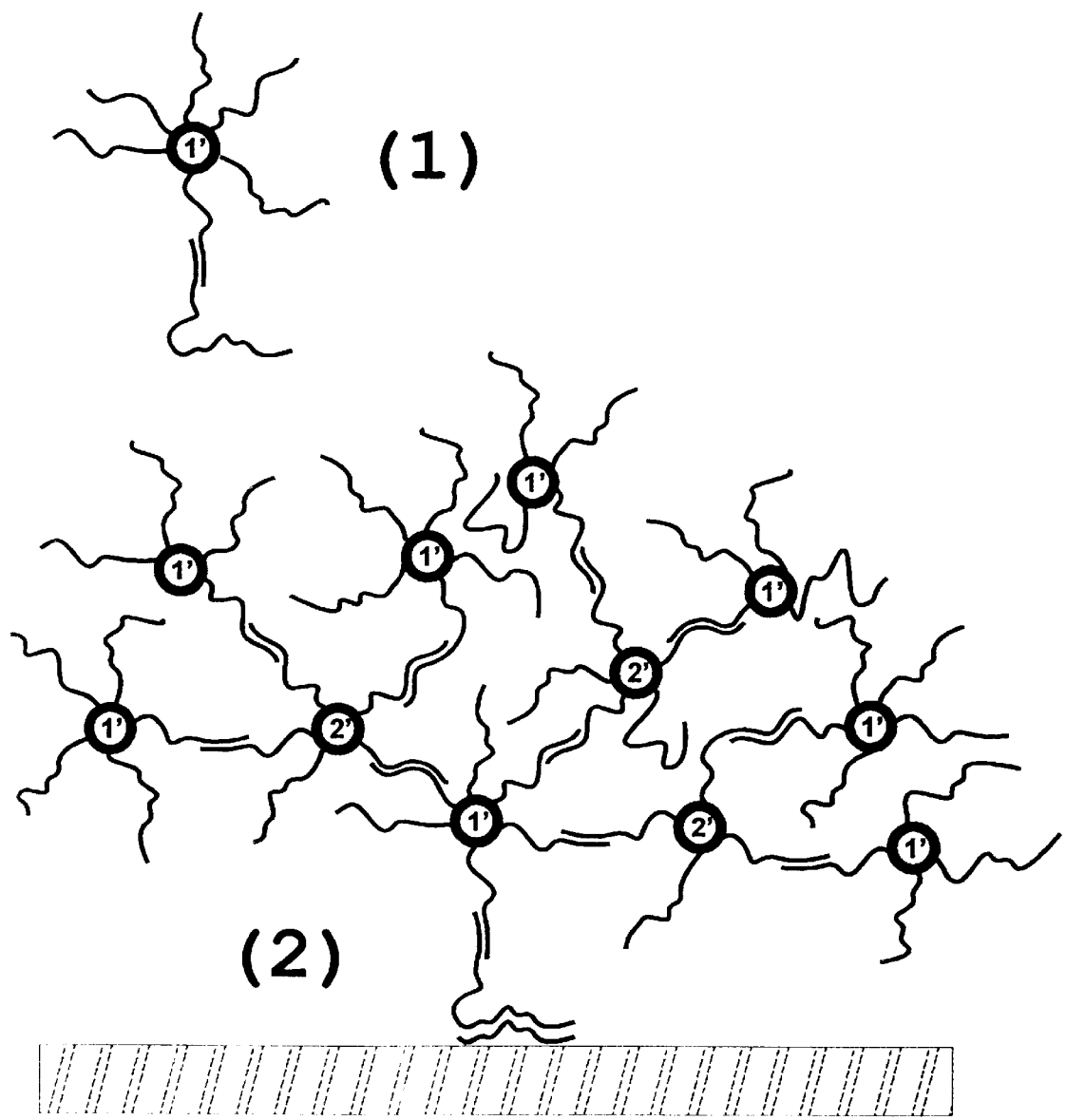
FIG. 7 is a schematic illustration showing use of a nucleic acid molecule linker which hybridizes to both a polynucleotide strand of a functionalized nanocrystal and to a molecular probe comprising an oligoncleotide, in operably linking the primary dot to the molecular probe; and showing dendrimer formation resulting from subsequent and successive additions of secondary dots and primary dots.

In another illustrative embodiment, and as shown in FIGS. 6A, 6B, and 7, a linker may be used to contact and operably link a functionalized nanocrystal to a molecular probe. For example, where both entities (the polynucleotide strand of the primary dots, and molecular probe) are thiolated, a homobifunctional linker may be used such as bismaleimidohexane. Where one entity has a reactive functionality comprising one or more thiol groups, and the other entity has a reactive functionality comprising one or more amino groups, heterobifunctional linkers may include, but are not limited to, sulfo-GMBS, sulfo-MBS, sulfo-SMCC, and sulfo-SMPB. In another variation of this embodiment, the molecular probe comprises an oligonucleotide probe which is first operably linked to the primary dots, and then added to the sample being analyzed for the presence or absence of the target molecule under conditions which promote contact and binding of the molecular probe to the target molecule, if present. Alternatively, as shown in FIG. 7, the linker may be a nucleic acid molecule which has, at one end comprising a terminal portion, a sequence complementary (for hybridizing) to the sequence of a terminal portion of the free end of a polynucleotide strand of the primary dot; and an opposite end or terminal portion which has a sequence which is sufficiently complementary (for hybridizing) to a portion of the molecular probe comprising an oligonucleotide. In this latter variation, conditions suitable for contact and hybridization may be used to either operably link the primary dot with molecular probe prior to the addition of the molecular probe to a sample being analyzed for the presence or absence of a target molecule, or to operably link the primary dot to the molecular probe after the molecular probe has already been added to the sample being analyzed under suitable conditions for the molecular probe to contact and bind to the target molecule, if present in the sample.

Figure 8:
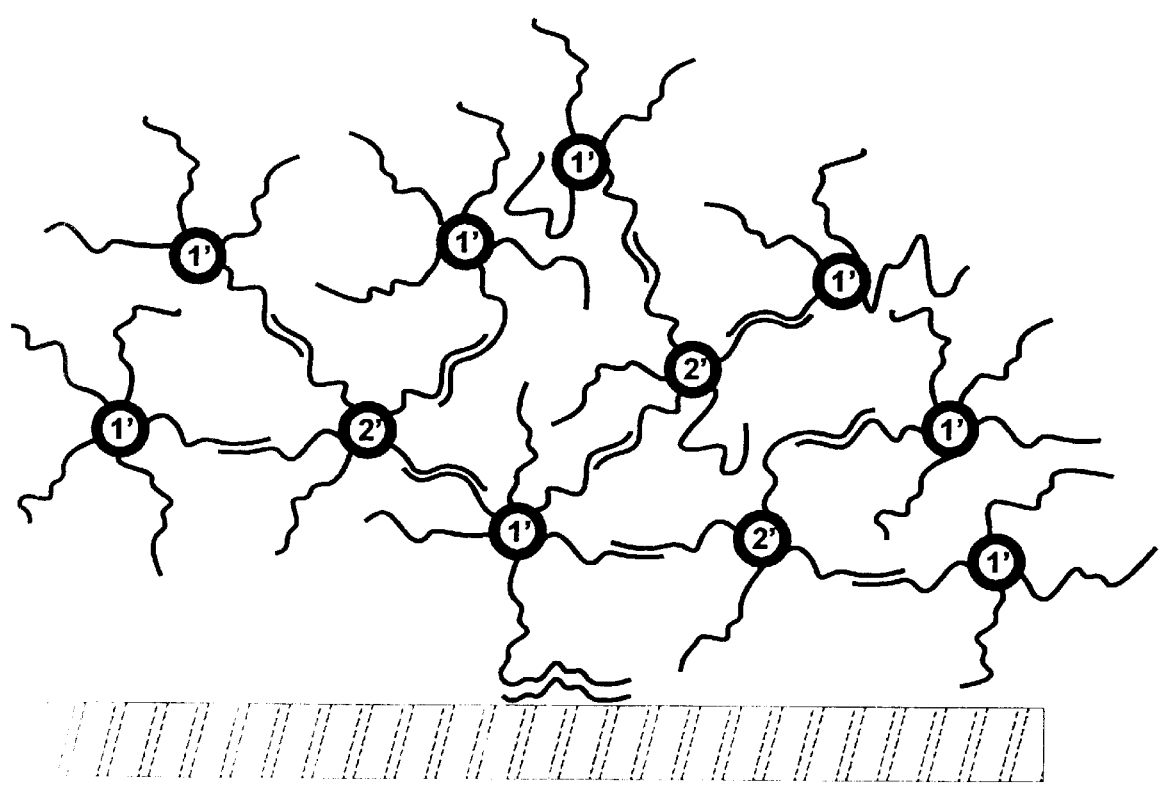
FIG. 8 is a schematic illustration showing a molecular probe which is incorporated or synthesized as part of a polynucleotide strand of a functionalized nanocrystal comprising a primary dot (wherein the molecular probe portion is shown here as bound to its target molecule); and showing dendrimer formation resulting from subsequent and successive additions of secondary dots and primary dots.

In another embodiment, as illustrated in FIG. 8, the molecular probe comprising an oligonucleotide is synthesized as part of the free end, at the terminal portion, of one or more of the plurality of polynucleotide strands of the primary dots, using methods known to those skilled in the art of nucleic acid molecule synthesis. This embodiment requires knowing the sequence of the oligonucleotide probe so as to be able to synthesize it as part of the polynucleotide strand; and thus, is unlike most of the other embodiments described herein for operably linking the molecular probe to the primary dots which rely on reactive functionalities other than nucleic acid complementarity. An effective amount of the primary dot of this embodiment is contacted with a sample under suitable conditions for the portion comprising the molecular probe to contact and bind (e.g., hybridize) to its target molecule (comprising a nucleic acid molecule with sequence complementary to the molecular probe sequence), if present, in the sample being analyzed for the presence or absence of the target molecule.

In summary, primary dots may be operably linked to molecular probe using means which include, but are not limited to, (a) by a reactive functionality on one or more of the plurality of polynucleotide strands and a reactive functionality associated with the molecular probe (see, e.g., FIG. 3); (b) by a reactive functionality on the coating of the primary dot and a reactive functionality associated with the molecular probe (see, e.g. FIGS. 4A and 4B); (c) by a linker which has one portion that binds to a reactive functionality on one or more polynucleotide strands, and another portion which binds to a reactive functionality associated with the molecular probe (see, e.g., FIG. 5); (d) by a linker which has one portion that hybridizes to one or more polynucleotide strands, and another portion which hybridizes to the molecular probe comprising a nucleic acid molecule (e.g., oligonucleotide) (see, e.g., FIG. 7); and (e) by synthesizing the molecular probe as part of one or more polynucleotide strands (see, e.g., FIG. 8).

EXAMPLE 5

In this example, illustrated are embodiments of the method of using functionalized nanocrystals comprising a plurality of polynucleotide strands according to the present invention for signal generation and signal amplification for detecting the presence or absence of a target molecule. The method uses successive additions of primary dots and secondary dots to a sample, wherein molecular probe bound to target molecule anchors primary dots and secondary dots in forming dendrimers that provide signal generation and amplification. In a preferred embodiment, "successive additions of primary dots and secondary dots" comprises at least one addition of each and may range up to, or greater than, 50 additions of each. For detecting the presence or absence of a target molecule in a sample, the method comprises a first step of operably linking primary dots to molecular probe in forming primary dot-molecular probe complexes, and then contacting an effective amount of primary dot-molecule probe complexes to the sample under suitable conditions for molecular probe to specifically bind to target molecule, if present in the sample. An alternative is to first contact an effective amount of molecular probe with the sample under suitable conditions for molecular probe to bind to target molecule, if present; and then contacting the sample with an effective amount of primary dots under suitable conditions for primary dots to operably link to molecular probe, if present in the sample. In either embodiment, the sample is then contacted with an effective amount of secondary dots under suitable conditions for promoting hybridization of the plurality of polynucleotide strands of the second dots to the polynucleotide strands of the primary dots, if present in the sample. The sample is then contacted with successive additions of an effective amount of primary dots and an effective amount of secondary dots under suitable conditions for promoting hybridization. The primary dots added in the successive additions may either lack or possess a reactive functionality (e.g., primary dots used in the first step may have one or more biotinylated polynucleotide strands that operably links to avidinylated molecular probe; however, the primary dots added after the first step and for forming dendrimers may comprise a plurality of polynucleotide strands that lack biotinylation). The sample is then exposed to an excitation light source that is suitable for exciting the functionalized nanocrystals to emit a fluorescence emission. Detection by detection means of a signal comprising peak fluorescence emission, generated by excited functionalized nanocrystals, and amplified in intensity by dendrimer formation, is indicative of the presence of target molecule in the sample (see, e.g., FIGS. 3–8); and absence of the signal is indicative of the absence of target molecule in the sample.

The method may further comprise one or more wash steps after each addition of functionalized nanocrystals to the sample to remove from the sample unbound or non-specifically bound functionalized nanocrystals (and unbound or non-specifically bound molecular probe). In a preferred embodiment, the primary dots and secondary dots comprise a uniform size such that after excitation, they each emit a fluorescence emission of a narrow bandwidth, which may be representative of a single color; and hence, the fluorescence intensity is amplified by dendrimer formation. Thus, the method may further comprise quantitating the amount of target molecule present in a sample by measuring the fluorescence intensity of the signal generated, and relating the amount of fluorescence intensity to an amount of target molecule. As previously described in more detail herein, the primary dots and the secondary dots can be excited with the same excitation light source. The excitation light source (visible, or UV, or a combination thereof) is preferably in the spectral range of from about 200 nm to about 500 nm; and in a more preferred embodiment, in a spectral range of from about 300 nm to about 400 nm. In a preferred embodiment, fluorescence peak emission comprises a discrete fluorescence peak in the spectral range of about 400 nm to about 750 nm. The fluorescence emission may be detected, or detected and quantitated, by appropriate detection means (e.g., one or more of: photodetector, filter, charge couple device camera (CCD camera) fluorescence microscope, fluorescence imaging microscope, a scanner or reader for detecting fluorescence, a fluorescence cube, a computer for processing detected fluorescence, and the like).

For example, CdSe/ZnS quantum dots having a substantially uniform size comprising a diameter of about 68.4 angstroms (A) may be excited with light of a spectral range of from about 400 nm to 500 nm, and emit a fluorescence peak (orange) at 609 nm. CdSe/ZnS quantum dots having a substantially uniform size comprising a diameter of about 53.2 A may be excited with light of a spectral range of from about 400 nm to 500 nm, and emit a fluorescence peak (yellow) at 545 nm. CdSe/ZnS quantum dots having a substantially uniform size comprising a diameter of about 46.6 A may be excited with light of a spectral range of from about 400 nm to 500 nm, and emit a fluorescence peak (green) at 522 nm. In a preferred embodiment, detection may be by detection means comprising a scanner or reader or other analytical instrument which can detect discrete fluorescence peaks in the spectral range of about 400 nm to about 750 nm; and, optionally (when more than one color is used in the method according to the present invention), distinguish between discrete fluorescence peaks within that spectral range. In the class of quantum dots used in the present invention, various sizes of dots can be excited with a single wavelength spectrum of light, resulting in many emissions of discrete fluorescence peaks corresponding to colors that can be detected simultaneously and distinctly. Thus, for example, it will be apparent to those skilled in the art that method of the present invention encompasses detection of more than one target molecule and/or use of more than one type or specificity of molecular probe simultaneously in the sample, by using a uniform size of functionalized nanocrystals which is different for each type or specificity of molecular probe used. For example, a first set of primary dots and secondary dots comprise a uniform size, wherein the primary dots comprise a plurality of polynucleotide strands which comprise SEQ ID NO:1, and the secondary dots comprise a plurality of polynucleotide strands comprising SEQ ID NO:2, and wherein the primary dots are operably linked to a molecular probe having binding specificity for a target molecule comprising "gene X". A second set of primary dots and secondary dots comprise a uniform size wherein the uniform size is different than the that of the first set (hence, will emit a separate, discrete fluorescence peak which can be distinguished from a fluorescence peak emitted from the first set), wherein the primary dots comprise a plurality of polynucleotide strands which comprise SEQ ID NO:3, and the secondary dots comprise a plurality of polynucleotide strands comprising SEQ ID NO:4, and wherein the primary dots are operably linked to a molecular probe having binding specificity for a target molecule comprising "gene Z". Hence, a sample may be simultaneously assayed for the presence or absence of gene X and gene Z by using both sets of primary and secondary dots. More particularly, if both gene X and gene Z are present, detected simultaneously and distinctly will be a color representative of the fluorescence emission generated by the functionalized nanocrystals of the first set, and a different color representative of the fluorescence emission generated by the functionalized nanocrystals of the second set, respectively.

Assay kits for the method of the present invention are also provided. In one preferred embodiment, the assay kit comprises (a) primary dots which comprise functionalized nanocrystals comprising a plurality of polynucleotide strands which comprise a known sequence, wherein the primary dots have one or more reactive functionalities; and (b) secondary dots which comprise functionalized nanocrystals comprising a plurality of polynucleotide strands which comprise a known sequence which is complementary to the sequence of the polynucleotide strands of the primary dots. The reactive functionalities of the primary dots may be used to operably link the primary dots to molecular probe either directly (i.e., reacts with the reactive functionalities of molecular probe) or indirectly (reacts with a linker that is used to link the primary dots to molecular probe). Thus, the kit may further comprise a linker for linking the primary dots to molecular probe. In a preferred embodiment, the primary dots and secondary dots comprise a uniform size. In another embodiment, the primary dots further comprise molecular probe which is operably linked to the primary dots. The kit may further comprise primary dots lacking reactive functionalities. The kit may further comprise a second set of primary dots and secondary dots, wherein the primary dots and secondary dots of the second set comprise a uniform size wherein the uniform size is different than the that of the first set, wherein the primary dots of the second set comprise a plurality of polynucleotide strands which are complementary in sequence to the plurality of polynucleotide strands of the secondary dots of the second set, and wherein the plurality of polynucleotide strands of the primary dots of the second set lack sufficient complementarity (thus, will not specifically hybridize) to the plurality of polynucleotide strands of the primary dots of the first set.

In another preferred embodiment, the assay kit comprises (a) primary dots which comprise functionalized nanocrystals comprising a plurality of polynucleotide strands which comprise a known sequence, wherein the primary dots have one or more reactive functionalities; (b) secondary dots which comprise functionalized nanocrystals comprising a plurality of polynucleotide strands which comprise a known sequence which is complementary to the sequence of the polynucleotide strands of the primary dots; and (c) a molecular probe. In a preferred embodiment, the primary dots and secondary dots comprise a uniform size. In another preferred embodiment, the molecular probe further comprises one or more reactive functionalities that may be used to operably link the molecular probe to the primary dots either directly (i.e., reacts with the reactive functionalities of the primary dots) or indirectly (reacts with a linker that is used to link the molecular probe to the primary dots). Thus, the kit may further comprise a linker for linking the primary dots to molecular probe. The kit may further comprise primary dots lacking reactive functionalities. The kit may further comprise a second set of primary dots and secondary dots, wherein the primary dots and secondary dots of the second set comprise a uniform size wherein the uniform size is different than the that of the first set, wherein the primary dots of the second set comprise a plurality of polynucleotide strands which are complementary in sequence to the plurality of polynucleotide strands of the secondary dots of the second set, and wherein the plurality of polynucleotide strands of the primary dots of the second set lack sufficient complementarity (thus, will not specifically hybridize) to the plurality of polynucleotide strands of the primary dots of the first set.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. An assay kit comprising:
   (a) primary dots, each of which comprises a functionalized nanocrystal comprising a plurality of polynucleotide strands of a predetermined sequence, wherein a terminal portion of each of the plurality of polynucleotide strands is operably linked to the functionalized nanocrystal, wherein the opposite terminus of each of the plurality polynucleotide strand is unbound to the functionalized nanocrystal and extends outwardly from the functionalized nanocrystal, and wherein the primary dots have one or more reactive functionalities; and
   (b) secondary dots each of which comprises a functionalized nanocrystal comprising a plurality of polynucleotide strands of a predetermined sequence which is complementary to and can under suitable conditions hybridize to the sequence of the polynucleotide strands of the primary dots, wherein a terminal portion of each of the plurality of polynucleotide strands is operably linked to the functionalized nanocrystal, and wherein the opposite terminus of each of the plurality polynucleotide strand is not bound to the functionalized nanocrystal and extends outwardly from the functionalized nanocrystal.

2. The assay kit according to claim 1, wherein the primary dots and secondary dots comprise a uniform size.

3. The assay kit according to claim 1, further comprising a linker for linking the primary dots to molecular probe.

4. The assay kit according to claim 1, further comprising a molecular probe.

5. The assay kit according to claim 4, wherein the molecular probe is operably linked to the primary dots.

6. The assay kit according to claim 1, further comprising a linker, and molecular probe.

7. The assay kit according to claim 1, further comprising primary dots which lack reactive functionalities.

8. The assay kit according to claim 1, wherein the primary dots and secondary dots comprise a first set; and wherein the assay kit further comprises a second set of primary dots and secondary dots, wherein the primary dots and secondary dots of the second set comprise a uniform size which is different than the uniform size of the primary dots and secondary dots of the first set, wherein the primary dots of the second set comprise a plurality of polynucleotide strands which are complementary in sequence to the plurality of polynucleotide strands of the secondary dots of the second set, and wherein the plurality of polynucleotide strands of the primary dots of the second set lack sufficient complementarity to specifically hybridize to the plurality of polynucleotide strands of the primary dots of the first set.

9. A method of using functionalized nanocrystals comprising primary dots and secondary dots for detecting the presence or absence of a target molecule in a sample, the method comprising:

(a) operably linking primary dots to molecular probe in forming primary dot-molecular probe complexes;

(b) contacting an effective amount of primary dot-molecule probe complexes to the sample under suitable conditions for molecular probe to specifically bind to target molecule, if present in the sample;

(c) contacting an effective amount of secondary dots with the sample under suitable conditions for promoting hybridization of the plurality of polynucleotide strands of the second dots to the polynucleotide strands of the primary dots, if present in the sample;

(d) contacting the sample with successive additions of an effective amount of primary dots and an effective amount of secondary dots under suitable conditions for promoting hybridization;

(e) exposing the sample to an excitation light source that is suitable for exciting the functionalized nanocrystals to emit a fluorescence emission;

wherein detection by detection means of a signal comprising peak fluorescence emission, generated by excited functionalized nanocrystals, and amplified by dendrimer formation, is indicative of the presence of target molecule in the sample; and absence of the signal is indicative of the absence of target molecule in the sample.

10. The method according to claim 9, further comprising a wash step after each addition of functionalized nanocrystals to the sample to remove unbound or non-specifically bound functionalized nanocrystals from the sample.

11. The method according to claim 9, wherein the primary dots and secondary dots comprise a uniform size.

12. The method according to claim 9, further comprising quantitating the amount of target molecule present in a sample by measuring the fluorescence intensity of the signal generated, and relating an amount of fluorescence intensity to an amount of target molecule.

13. The method according to claim 9, wherein the excitation light source comprises a spectral range of from about 200 nanometers to about 500 nanometers.

14. The method according to claim 9, wherein the excitation light source comprises a spectral range of from about 300 nanometers to about 400 nanometers.

15. The method according to claim 9, wherein the fluorescence emission is in the spectral range of about 400 nanometers to about 750 nanometers.

16. A method of using functionalized nanocrystals comprising primary dots and secondary dots for detecting the presence or absence of a target molecule in a sample, the method comprising:

(a) contacting an effective amount of molecule probe to the sample under suitable conditions for molecular probe to specifically bind to target molecule, if present in the sample;

(b) contacting an effective amount of primary dots to the sample under suitable conditions for the primary dots to operably link to molecular probe, if present in the sample;

(c) contacting an effective amount of secondary dots with the sample under suitable conditions for promoting hybridization of the plurality of polynucleotide strands of the second dots to the polynucleotide strands of the primary dots, if present in the sample;

(d) contacting the sample with successive additions of an effective amount of primary dots and an effective amount of secondary dots under suitable conditions for promoting hybridization;

(e) exposing the sample to an excitation light source that is suitable for exciting the functionalized nanocrystals to emit a fluorescence emission;

wherein detection by detection means of a signal comprising peak fluorescence emission, generated by excited functionalized nanocrystals, and amplified by dendrimer formation, is indicative of the presence of target molecule in the sample; and absence of the signal is indicative of the absence of target molecule in the sample.

17. The method according to claim 16, further comprising a wash step after each addition of functionalized nanocrystals to the sample to remove unbound or non-specifically bound functionalized nanocrystals from the sample.

18. The method according to claim 16, wherein the primary dots and secondary dots comprise a uniform size.

19. The method according to claim 16, further comprising quantitating the amount of target molecule present in a sample by measuring the fluorescence intensity of the signal generated, and relating an amount of fluorescence intensity to an amount of target molecule.

20. The method according to claim 16, wherein the excitation light source comprises a spectral range of from about 200 nanometers to about 500 nanometers.

21. The method according to claim 16, wherein the excitation light source comprises a spectral range of from about 300 nanometers to about 400 nanometers.

22. The method according to claim 16, wherein the fluorescence emission is in the spectral range of about 400 nanometers to about 750 nanometers.

* * * * *